United States Patent
Ozaki et al.

(10) Patent No.: US 6,575,717 B2
(45) Date of Patent: Jun. 10, 2003

(54) MAGNETICALLY LEVITATED PUMP

(75) Inventors: Takayoshi Ozaki, Iwata (JP); Minoru Suzuki, Iwata (JP)

(73) Assignees: NTN Corporation, Osaka (JP); Terumo Kabushiki Kaisha, Tokyo (JP)

(*) Notice: Subject to any disclaimer, the term of this patent is extended or adjusted under 35 U.S.C. 154(b) by 0 days.

(21) Appl. No.: 09/748,274

(22) Filed: Dec. 27, 2000

(65) Prior Publication Data

US 2001/0016170 A1 Aug. 23, 2001

(30) Foreign Application Priority Data

Dec. 27, 1999 (JP) .......................................... 11-370953
Dec. 27, 1999 (JP) .......................................... 11-370954

(51) Int. Cl.$^7$ .......................... F04B 17/00; F04B 35/04; H02K 7/09
(52) U.S. Cl. .................. 417/420; 417/423.12; 310/90.5
(58) Field of Search ............................ 417/420, 423.12; 310/90.5

(56) References Cited

U.S. PATENT DOCUMENTS

| | | | |
|---|---|---|---|
| 3,107,310 A | * 10/1963 | Carriere et al. ............. 310/103 |
| 3,694,041 A | * 9/1972 | Studer ......................... 310/90.5 |
| 4,353,602 A | * 10/1982 | Habermann ................... 308/10 |
| 4,589,822 A | * 5/1986 | Clausen et al. .............. 277/397 |
| 4,688,998 A | * 8/1987 | Olsen et al. ................. 417/356 |
| 4,840,501 A | * 6/1989 | Wong et al. ............... 101/93.05 |
| 5,112,202 A | * 5/1992 | Oshima et al. ............. 415/900 |
| 5,350,283 A | * 9/1994 | Nakazeki et al. .......... 310/90.5 |
| 5,470,208 A | 11/1995 | Kletschka |
| 5,695,471 A | 12/1997 | Wampler |
| 5,725,357 A | * 3/1998 | Nakazeki et al. .............. 417/18 |
| 5,856,719 A | * 1/1999 | De Armas ................... 310/103 |
| 5,947,703 A | * 9/1999 | Nojiri et al. ................. 415/229 |

FOREIGN PATENT DOCUMENTS

| WO | WO 96/31934 | 10/1996 |
| WO | WO 97/42413 | 11/1997 |

OTHER PUBLICATIONS

The Random House College Dictionary (Revised Edition), 1984 Random House Inc. New York N.Y. p. 244.*

* cited by examiner

*Primary Examiner*—Charles G. Freay
*Assistant Examiner*—Timothy P. Solak
(74) *Attorney, Agent, or Firm*—McDermott, Will & Emery (57) ABSTRACT

A pump portion is provided with an impeller internal to a casing. The impeller is coupled with a rotor physically out of contact therewith and it is also supported by a controlled, magnetic bearing portion physically out of contact therewith. The impeller is rotated by a motor to discharge fluid. A position sensor detects the impeller position in levitation and in response to the sensor's output the magnetic bearing portion is controlled. The magnetic bearing portion is configured of a plurality of electromagnets formed of a magnetic pole, a yoke and a coil. The electromagnet has magnetic S and N poles each with at least yoke and coil arranged circumferentially.

11 Claims, 7 Drawing Sheets

XIB — XIB CROSS SECTION

IB—IB CROSS SECTION

XIB—XIB CROSS SECTION

XIIIB—XIIIB CROSS SECTION

MAGNETICALLY LEVITATED PUMP

BACKGROUND OF THE INVENTION

1. Field of the Invention

The present invention relates to magnetically levitated (maglev) pumps. More specifically, the present invention relates to those corresponding to a cleanpump employing a magnetic bearing and used for medical equipment, such as artificial heart.

2. Description of the Background Art

Figure 8A:
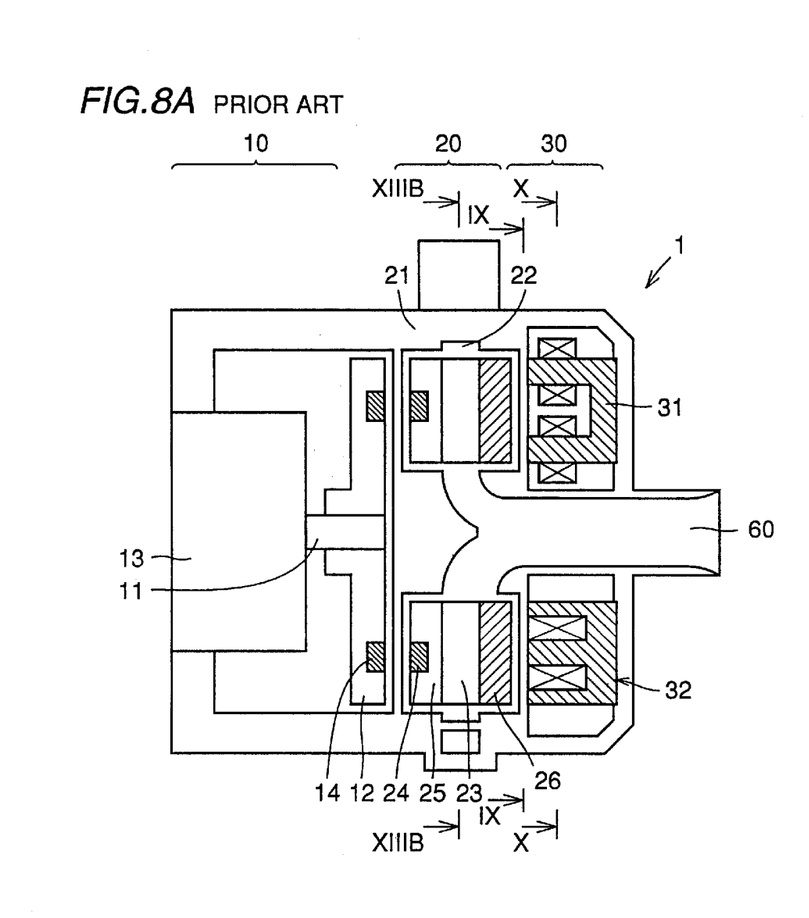
FIGS. 8A and 8B show a conventional maglev pump.
Figure 8B:
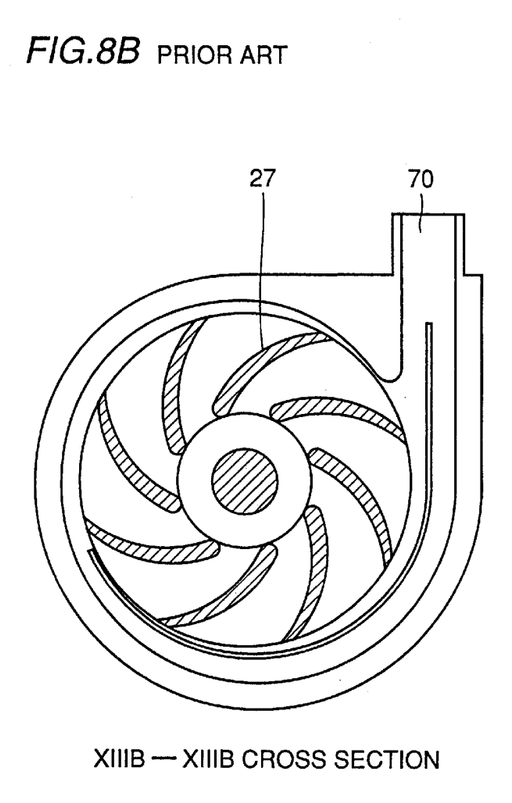
Figure 9:
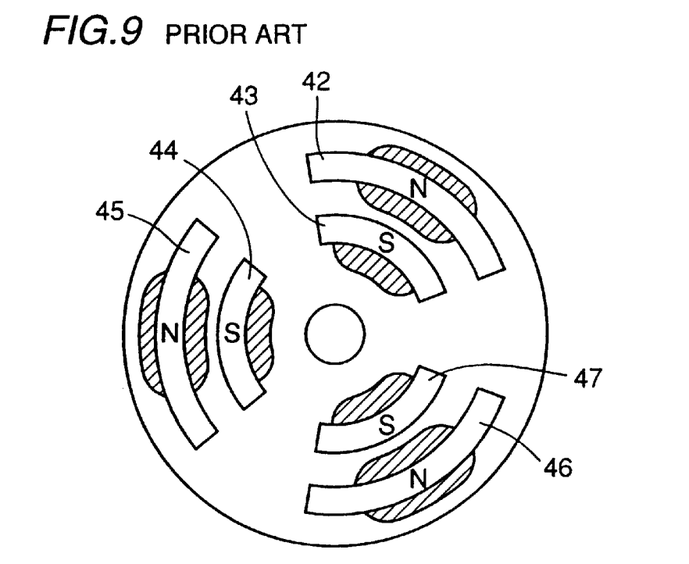
FIG. 9 is a cross section taken along line IX—IX of FIG. 8A.
Figure 10:
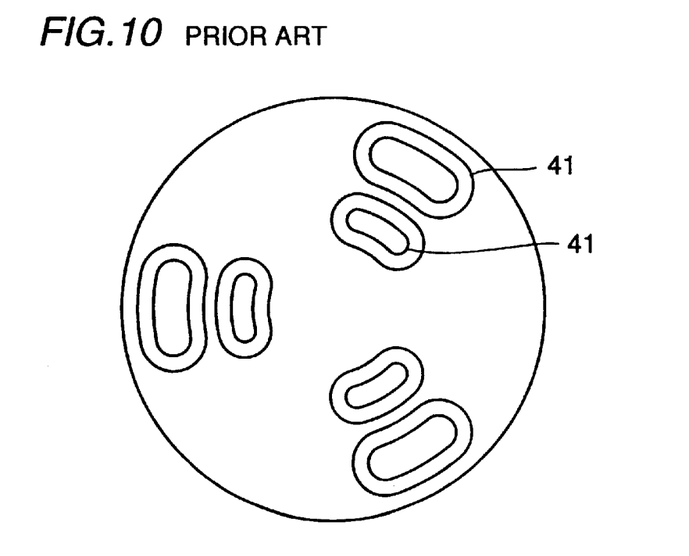
FIG. 10 is a cross section taken along line X—X of FIG. 8A.

FIGS. 8A and 8E, show a conventional maglev pump. More specifically, FIG. 8A is a vertical cross section thereof and FIG. 8B is a cross section taken along a line XIIIB—XIIIB of FIG. 8A. FIG. 9 is a cross section taken along a line IX—IX of FIG. 8A. FIG. 10 is a cross section taken along a line X—X of FIG. 8A.

Initially, with reference to FIG. 8*a* through FIG. 10, a conventional maglev pump will be described. As shown in FIG. 8A, a maglev pump 1 includes a motor portion 10, a pump portion 20 and a magnetic bearing portion 30. In pump portion 20, a casing 21 accommodates a pump chamber 22 in which an impeller 23 rotates. Impeller 23 has a plurality of vanes 27 spirally provided, as shown in FIG. 8B. Casing 21 is formed of a cylindrical, non-magnetic member and impeller 23 includes a non-magnetic member 25 having a permanent magnet 24 configuring a non-controlled magnetic bearing and a soft magnetic member 26 corresponding to a rotor of a controlled magnetic bearing. Permanent magnet 24 is divided in a circumferential direction of impeller 23 and magnets adjacent to each other are magnetized to have opposite magnetic poles.

Opposite to the side of impeller 23 provided with permanent magnet 24, external to pump chamber 22 there is provided a disk rotor 12 supported by a shaft 11. Rotor 12 is rotatably driven by a motor 13. Rotor 12 is provided with the same number of permanent magnets 14 as impeller 23 that face permanent magnet 24 of impeller 23 to provide attraction. Adjacent permanent magnets 14 are magnetized to have opposite magnetic poles.

Furthermore, opposite to the side of impeller 23 provided with soft magnetic member 26, an electromagnet 31 and a position sensor (not shown) are provided in magnetic bearing portion 30. Electromagnet 31 and the position sensor allow balance with the attraction of permanent magnets 24 and 14 to hold impeller 23 at the center of pump chamber 22.

In maglev pump 1 thus configured, attraction acts between permanent magnet 14 (embedded in rotor 12 and permanent magnet 24 provided in impeller 23, axially in one direction. This attraction is exploited to provide magnetic-coupling to rotatably drive impeller 23 and obtain radial supporting-stiffness. To match it to this attraction, a flow of current is passed through a coil of C-shaped electromagnet 31, which in turn attracts impeller 23 axially in the other direction to levitate impeller 23. As rotor 12 is rotatably driven by motor 13, permanent magnets 14 and 24 provide magnetic-coupling, impeller 23 rotates and a fluid is sucked through an inlet 60 and discharged through an outlet 70 (see FIG. 8B). Impeller 23 is accommodated in casing 21 and thus isolated from rotor 12 and it is also not contaminated by electromagnet 31. Thus, maglev pump 1 delivers fluid (blood if it is used as a blood pump) held clean.

Note that as shown in FIGS. 9 and 10, a conventional maglev blood pump has electromagnet 31 with an arcuate yoke 41 and pairs of magnetic poles 42 and 43, 44 and 45, and 46 and 47 each arranged radially.

If maglev pump as shown in FIGS. 8A and 8B is used as a blood pump for an artificial heart, it is implanted in a body or used adjacent thereto. As such, it cannot be supplied with energy constantly from an external power supply. Typically, it is supplied with energy obtained from a mobile battery or a battery implanted in the body. As such, to use it for a long term, energy consumption must be minimized. Furthermore, if it is used for human body, it is required to have a small size and it also must be taken great care of to be reliable.

Conventional maglev pump 1, however, as shown in FIGS. 9 and 10, has each electromagnet with magnetic poles arranged radially. As such, the space for accommodating the coil cannot be effectively obtained. As such, magnetic bearing portion 30 must be disadvantageously increased in size to provide an additional space for the coil to reduce the power consumption of the electromagnet.

More specifically, while the power consumption of the electromagnet is reduced by increasing the winding count of the electromagnet coil or increasing the diameter of the wire of the coil, either technique requires increasing magnetic bearing portion 30 in size to ensure a large space for accommodating the coil. Furthermore, conventional maglev pump 1 has electromagnet 31 with an arcuate yoke. This makes it difficult to wind the coil and also hardly ensures insulation resistance between the coil and the yoke.

Furthermore, as shown in FIGS. 8A and 8B, maglev pump 1 has a partition corresponding to casing 21 of plastic material, ceramic material or nonmagnetic metal material provided between soft magnetic member 26 of impeller 23 in pump chamber 22 and electromagnet 31 of magnetic bearing portion 30 and between soft magnetic member 26 of impeller 23 and position sensor 32 detecting the position of impeller 23. As such, impeller 23 and electromagnet 31 are spaced far apart from each other. Thus, to levitate impeller 23 electromagnet 31 is required to pass a large amount of current. Furthermore, the sensor sensitivity also degrades as impeller 23 and position sensor 32 are spaced far apart from each other.

More specifically, if the partition is formed of plastic material, the partition is less durable and can thus not be used for a long term. If the partition is formed of metal material and position sensor 32 is a magnetic sensor, then it has eddy current generated internal thereto to result in a loss and it also degrades the sensor sensitivity as it spaces position sensor 32 apart from a target.

SUMMARY OF THE INVENTION

Therefore the present invention mainly contemplates a maglev pump capable of miniaturizing a magnetic bearing portion.

The present invention also contemplates a maglev pump capable of reducing the distance between an electromagnet and an impeller and also reducing the distance between a sensor and the impeller to reduce the electromagnet's coil current and enhance the sensitivity of the sensor output.

The present invention generally provides a maglev pump wherein a pump portion is provided with a rotative portion internal to a casing, the rotative portion is coupled with a rotation driving portion physically out of contact therewith and it is also supported by a controlled, magnetic bearing portion physically out of contact therewith, the rotative portion is rotated by the rotation driving position to discharge fluid, a position sensor detects the position of the rotative portion in levitation and in response to the output of the position detection portion the controlled magnetic bearing portion is controlled, wherein the magnetic bearing portion is configured of a plurality of electromagnets formed of a magnetic pole, a yoke and a coil and the electromagnet has magnetic S and N poles each with at least the yoke and coil arranged circumferentially.

As such in an embodiment of the present invention a magnetic bearing includes electromagnets each having a magnetic pole and a yoke that are arranged circumferentially. This ensures a large space for winding a coil without increasing the space for the magnetic bearing portion or increasing the size of the pump. Since the coil can be accommodated in such a large space, the electromagnet coil can have an increased winding count and an increased wire diameter and consequently its power consumption can be reduced. Furthermore, the electromagnet can have a yoke in the form of a cylinder or a prism to facilitate winding a coil and thus readily ensure the insulation withstand voltage between the coil and the yoke.

More preferably, the electromagnet has a pair of magnetic poles circumferentially arranged and the electromagnet has a pair of magnetic poles radially arranged.

Still more preferably, the rotative portion is provided in a form of a disk having a side facing the rotation driving portion and provided with a permanent magnet circumferentially arranged and the rotative portion and the rotation driving portion are magnetically coupled together physically out of contact with each other, and the electromagnet has three pairs of magnetic S and N poles.

Furthermore the present invention in another aspect provides a maglev pump wherein a pump portion is provided with a rotative portion internal to a casing, the rotative portion is coupled with a rotation driving portion physically out of contact therewith and it is also supported by a controlled, magnetic bearing portion physically out of contact therewith, the rotative portion is rotated by the rotation driving portion to discharge fluid, a position sensor detects the position of the rotative portion in levitation and in response to the output of the position detection portion the controlled magnetic bearing portion is controlled, wherein the magnetic bearing portion includes a plurality of electromagnets each directly facing the rotative portion or the position detection portion includes a magnetic sensor directly facing the rotative portion.

Thus in the present invention the magnetic bearing portion can have a plurality of electromagnets directly facing a rotative portion or a magnetic sensor directly facing the rotative portion to reduce the distance between the rotative portion and the electromagnets or the magnetic sensor corresponding to a plane in which the electromagnetic force of the magnetic bearing acts. Thus, the pump can be levitated with a reduced amount of current flowing through an electromagnet coil for generating electromagnetic force to levitate the same, which is advantageous when the present pump is used as a blood pump since current consumption is one of its significant issues. Furthermore, the position sensor can be enhanced in sensitivity.

More preferably, the position detection portion includes a core formed of a soft magnetic material and a coil wound around the core.

Still more preferably, any of the electromagnet and the position detection portion is flipped to the casing by any of welding, brazing, press-fitting, pressure-welding, shrink-fitting and bonding or a combination thereof.

Still more preferably, the rotative portion is provided in the form of a disk having a side facing the rotation driving portion and having a first permanent magnet circumferentially arranged and the rotation driving portion has a second permanent magnet circumferentially arranged to face the first permanent, magnet, the first and second permanent magnets achieving magnetic-coupling to couple together the rotative portion and the rotation driving portion physically out of contact with each other, and the pump portion has an internal surface coated with heparin.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Reference will now be made to FIG. 1A through FIG. 3 to describe a maglev pump in one embodiment of the present invention. The maglev pump is configured of a motor portion 10, a pump portion 20 and a magnetic bearing portion 40. In pump portion 20 a casing 21 houses a pump chamber 22 in which an impeller 23 rotates. Impeller 23 has a plurality of vanes 27 provided spirally, as shown in FIG. 1B.

Figure 1A:
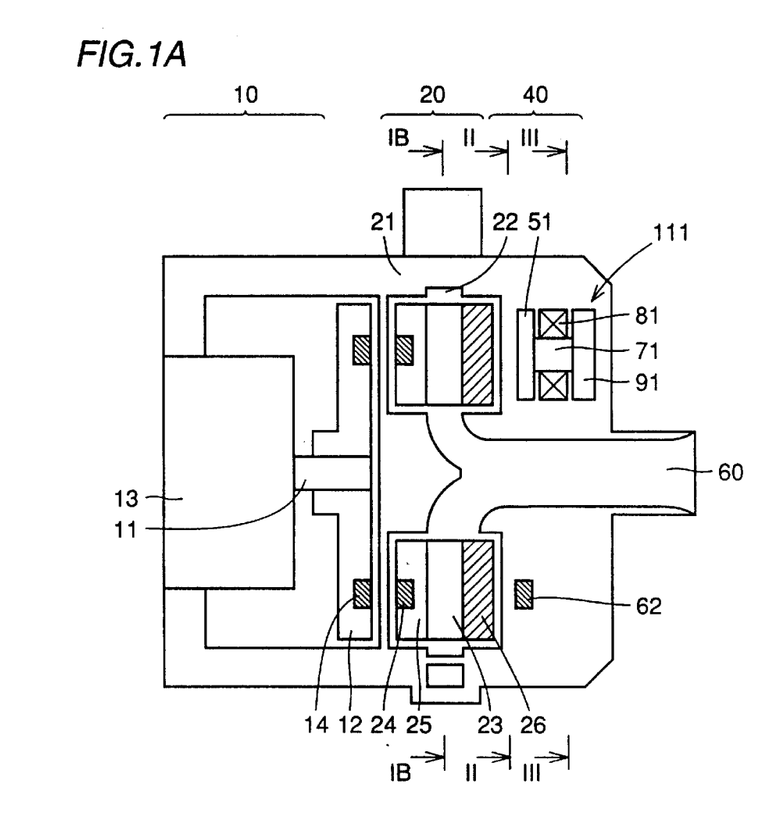
FIGS. 1A and 1B show a maglev pump in one embodiment of the present invention.
Figure 1B:
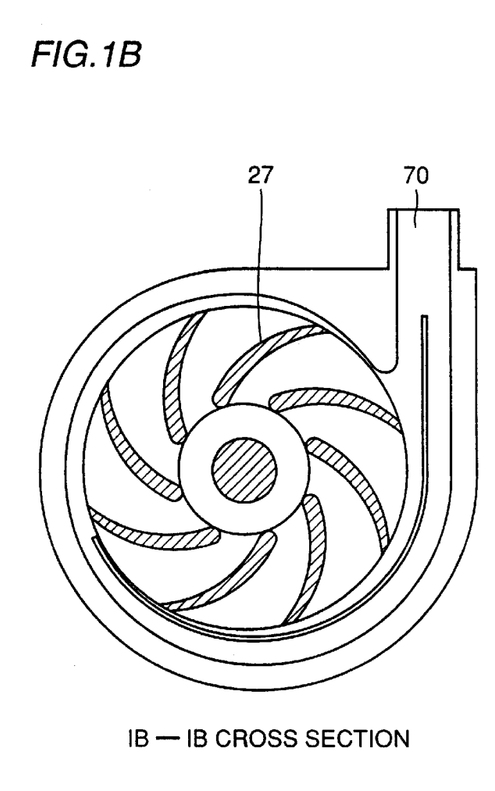

Casing 21 is formed of plastic, ceramic, metal or the like, although magnetic material cannot be used for casing 21 corresponding to a partition located between pump portion 20 and motor portion 10 and that located between pump portion 20 and magnetic bearing portion 40 and nonmagnetic material is thus used to form those partitions. Impeller 23 includes a nonmagnetic member 25 having a permanent magnet 24 configuring a non-controlled magnetic bearing, and a soft magnetic member 26 corresponding to a rotor of a controlled magnetic bearing. Permanent magnet 24 is divided in a circumferential direction of impeller 23 and adjacent permanent magnets are magnetized to have opposite magnetic poles.

Note that in FIG. 1A a hatched portion corresponds to a soft magnetic material and the remaining portion corresponds to a nonmagnetic material. If the pump is used for transferring a corrosive fluid such as blood, the soft magnetic material is preferably, e.g., highly corrosive-resistant, ferritic stainless steel (corresponding to JIS G4303

SUS447J1 and JIS G4303 SUS444) and the nonmagnetic material is preferably, e.g., highly corrosive-resistant austenitic stainless steel (corresponding to SUS316L or the like), or titanium alloy, pure titanium or the like.

Opposite to the side of impeller 23 provided with permanent magnet 24, external to the pump chamber there is provided a rotor 12 supported by a shaft 11. Rotor 12 is rotatably driven by a motor 13. Rotor 12 is provided with the same number of permanent magnets 14 as impeller 23 that face permanent magnet 24 of impeller 23 to provide attraction. Permanent magnets 14 adjacent to each other are magnetized to have opposite magnetic poles. Motor portion 10 is a synchronous motor including a DC brushless motor, an asynchronous motor including an induction motor, or the like, although any type of motor may be used.

Opposite to the side of impeller 23 provided with soft magnetic member 26, an electromagnet 111 and a position sensor 62 are provided in magnetic bearing portion 40. Electromagnet 111 and position sensor 62 allow balance with the attraction of permanent magnets 24 and 14 to hold impeller 23 at the center of the pump chamber.

Figure 2:
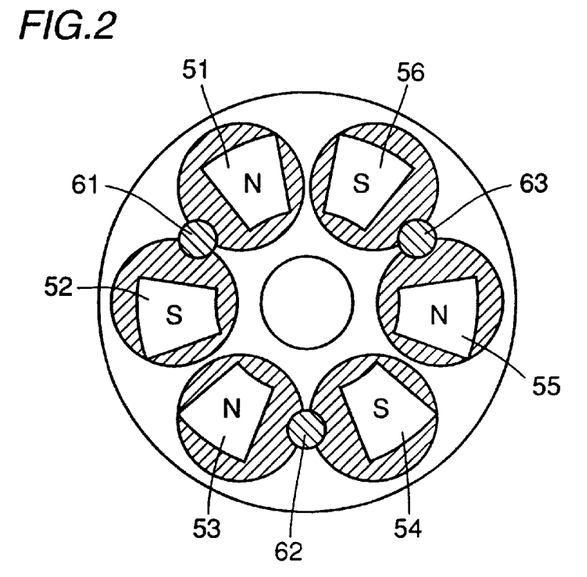
FIG. 2 is a cross section taken along line II—II of FIG. 1A.

FIG. 1A shows a single electromagnet 111 configured of a magnetic pole 51, an electromagnet yoke 71, an electromagnet coil 81 and an electromagnet backplate 91, although magnetic bearing portion 40 has three electromagnets arranged circumferentially. Furthermore, as shown in FIG. 2, sensors 61, 62 and 63 are arranged between their respective pairs of magnetic poles 51 and 52, 53 and 54, and 55 and 56. Sensors 61 to 63 are typically a magnetic sensor, such as an eddy-current sensor, a reluctance sensor, or the like.

Figure 3:
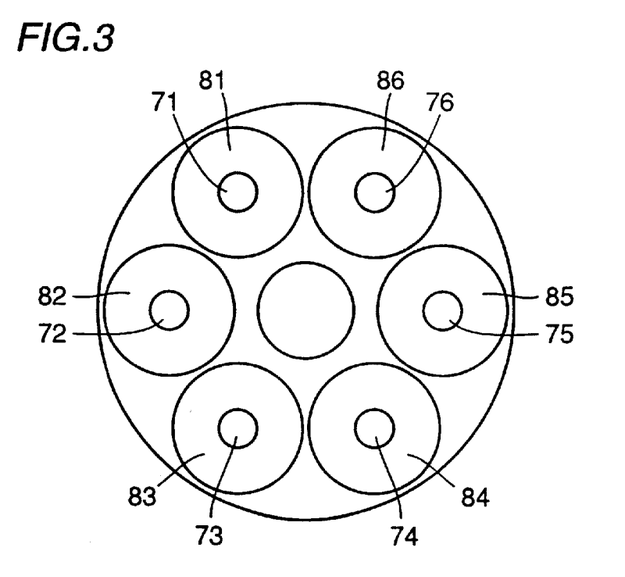
FIG. 3 is a cross section taken along line III—III of FIG. 1A.

Furthermore, as shown in FIG. 3, electromagnet yokes 71 to 76 each has a cylindrical shape, with electromagnet coils 81 to 86 wound therearound, respectively.

Circumferentially arranging magnetic poles 51–56 can increase a space for accommodating electromagnet coils 81 to 86 that can be housed in magnetic bearing portion 40. Furthermore, providing electromagnet yokes 71 to 76 in the form of a cylinder can facilitate winding electromagnet coils 81 to 86 around electromagnet yokes 71 to 76. Furthermore, electromagnet yokes 71 to 76 having a simple shape ensures reliable isolation from electromagnet coils 81 to 86.

Although electromagnet yokes 71 to 76 are provided in the form of a cylinder, they may be provided in the form of a prism. Furthermore, while in FIGS. 2 and 3 electromagnet yokes 71 to 76 and electromagnet coils 81 to 86 are arranged on a single circumference, they may not be arranged on a single circumference so that an accommodating space can be effectively ensured.

Figure 4:
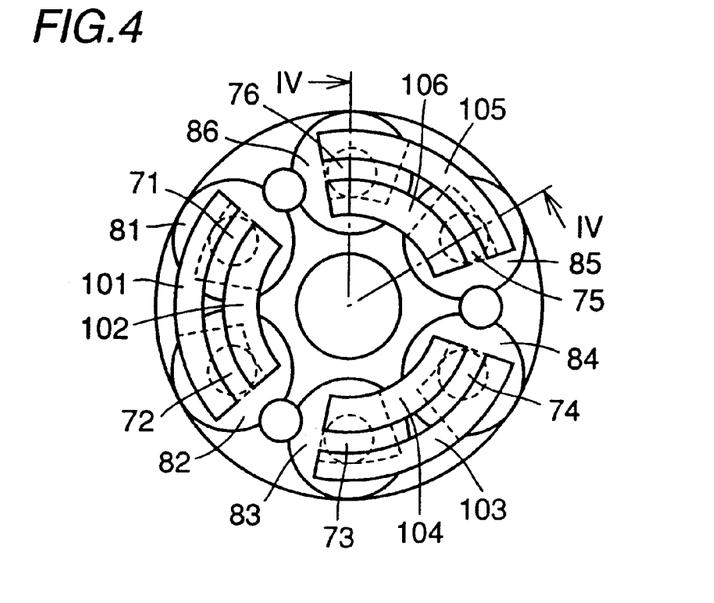
FIG. 4 shows another embodiment of the present invention, showing an exemplary arrangement of a magnetic pole and a coil.
Figure 5:
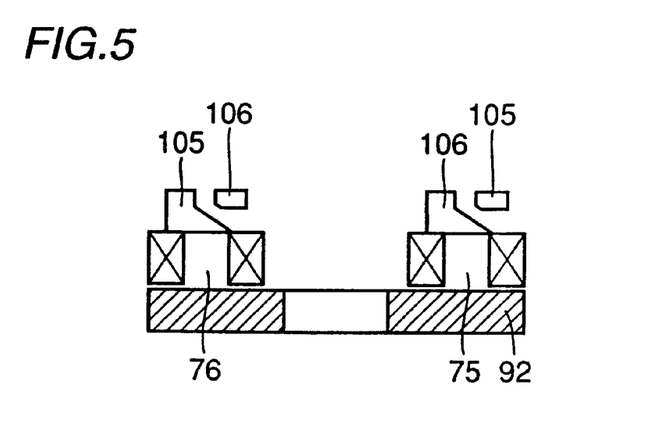
FIG. 5 is a cross section taken along line IV—IV of FIG. 4.

FIGS. 4 and 5 show another embodiment of the present invention, and FIG. 4 shows an exemplary arrangement of a magnetic pole and a coil and FIG. 5 is a cross section taken along line IV—IV of FIG. 4.

In FIG. 4, electromagnet coils 81 to 86 and electromagnet yokes (not shown) are arranged circumferentially, as similarly in FIG. 3, although pairs of magnetic poles 101 and 102, 103 and 104, and 105 and 106 are each arranged radially. Furthermore, as shown in FIG. 5, magnetic pole 105, electromagnet yoke 75, electromagnet backplate 92, electromagnet yoke 76 and magnetic pole 106 configure a single C-shaped electromagnet. The embodiment shown in FIGS. 4 and 5 also has an electromagnet yoke in the form of a cylinder to facilitate winding electromagnet coils 81 to 86, although the yoke is not limited to the cylinder and it may for example be a prism.

The present embodiment is as effect as the embodiment shown in FIG. 1A through FIG. 3.

Figure 6A:
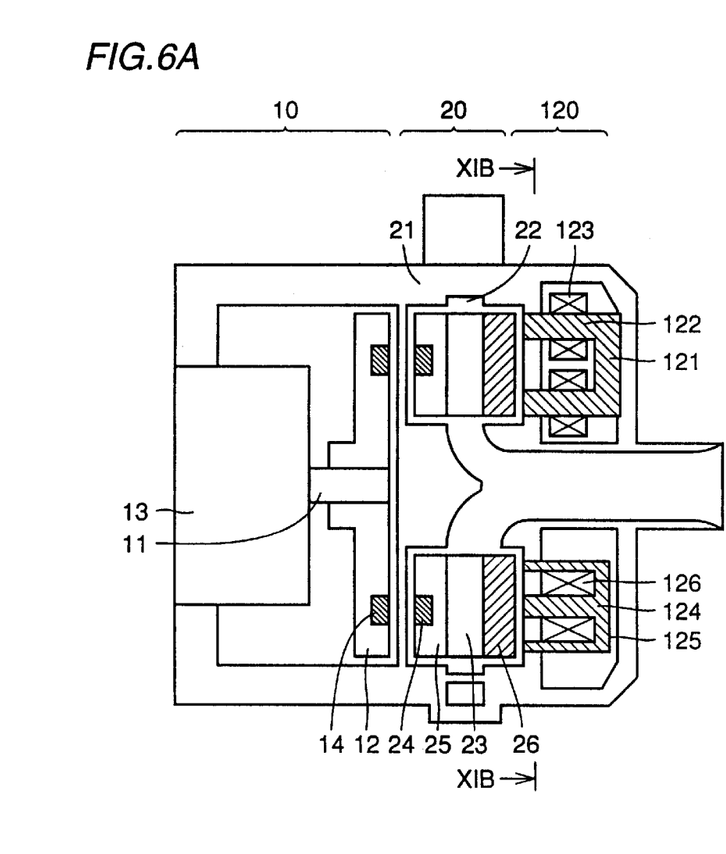
FIGS. 6A and 6B show another embodiment of the present invention.
Figure 6B:
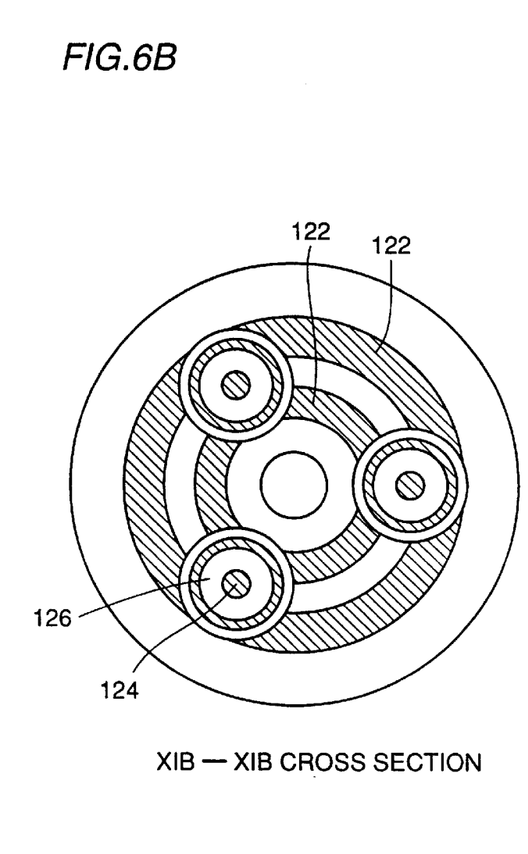

FIGS. 6A and 6B show another embodiment of the present invention, and FIG. 6A is a vertical cross section and FIG. 6B is a cross section taken along line XIB—XIB of FIG. 6A.

In the present embodiment, a magnetic bearing portion 120 includes an electromagnet 121 having a core 122 and a position sensor 124 having a core 125 and cores 122 and 125 are partially buried in casing 21 formed of a nonmagnetic material and providing a partition between magnetic bearing portion 120 and pump portion 20. Core 122 has a coil 123 wound therearound and core 125 has a coil 126 wound therearound. Furthermore, electromagnet 121 and position sensor 124 have their respective ends exposed in pump chamber 22. Electromagnet 121 and casing 21 of pump chamber 22 are welded, brazed, press-fit, pressure-welded, shrink-fit or bonded together, or jointed together by a combination of those techniques to seal the interior and exterior of pump chamber 22. Furthermore, to provide biocompatibility to the portion welded, brazed, press-fit, pressure-welded, shrink-fit or bonded as above, pump chamber 2 can have its interior entirely coated with heparin serving as an anticoagulant to prevent thrombus formation to allow the pump to be used as a blood transporting pump. In this example, heparin coating effectively constrains activation of coagulation system, protects platelets, constrains activation, activation of inflammation system, activation of fibrinolysis system, and the like.

As has been described above, in the present embodiment, electromagnet 121 and position sensor 124 have their respective ends exposed in pump chamber 22 to directly face impeller 23. This can reduce the distance between soft magnetic member 25 of impeller 23 in pump chamber 22 and position sensor 124 detecting the position of the impeller. As a result, impeller 23 can be levitated with a small amount of current flowing through the coil of electromagnet 21 and position sensor 124 can also be enhanced in sensitivity.

Figure 7:
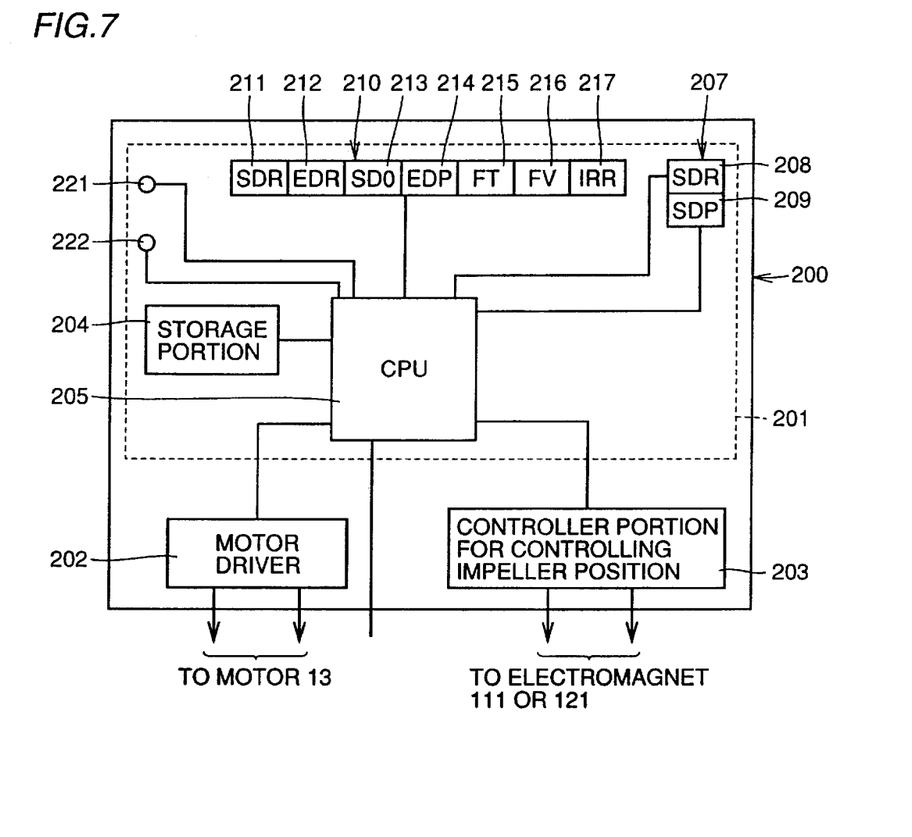
FIG. 7 is a block diagram of a controller for driving a maglev pump of the present invention.

FIG. 7 is a block diagram showing a controller for driving a maglev pump of the present invention. In FIG. 7, a controller 200 includes a function provided to control the position of the impeller, a function provided to control the running torque of the impeller, a function employing the function controlling the impeller position, to alter in pump chamber 22 the position of impeller 23 in levitation, a function provided to measure the current of motor 13, and a function provided to calculate a fluid viscosity by referring to a variance of the current of motor 13 measured when the position of impeller 23 in levitation is changed via the function controlling the impeller position in levitation.

More specifically, controller 200 includes a controller body 201, a motor driver 202, and a control portion 203 for controlling the impeller position. Motor driver 202 outputs a level of voltage corresponding to a motor rotation rate output from controller body 201, to rotate motor 13. Furthermore, control portion 203 for controlling the impeller position maintains the impeller position in levitation output from controller body 201, by controlling the current or voltage flowing through the FIG. 1A electromagnet 111 or the FIG. 6A electromagnet 121. The FIG. 2 position sensor 61 to 63 or the FIG. 6A position sensor 24 output a result of detection, which is in turn input to control portion 203 for controlling the impeller position, to control the current flowing through electromagnet 111 or 121, to control the translation of impeller 23 in the direction of the central axis (an axis z) and the rotation of impeller 23 around axes x and y orthogonal to the central axis (axis z). Note that the position sensor 61–63 or 124 output may be input to controller body 201, which may in turn output a value of voltage or current applied to electromagnet 111 or 121.

Controller body 201 includes a storage portion (ROM) 204, a CPU 205 with input and output terminals 221, 222, a display portion 210 and an input portion 207. Display portion 210 includes a set delivery rate (SDR) display portion 211, an executed delivery rate (EDR) display portion 212, a set delivery output (SDO) display portion 213, an executed delivery pressure (EDP) display portion 214, a fluid temperature (FT) display portion 215, a fluid viscosity (FV) display portion 216, and an impeller rotation rate (IRR) display portion 217. Furthermore, input portion 207 includes an SDR input portion 208 and an SDP input portion 209.

Controller body 201 includes a data storage portion storing data of a relationship between fluid viscosity and motor current variance, corresponding to a previously obtained relationship between fluid viscosity and motor current variance depending on position variance the impeller in levitation (variance in motor drive current), or a relationship expression calculated from the data related to such relationship (for example data of a correlation expression or data of an expression of viscosity calculation), and the function provided for calculation of fluid viscosity calculates fluid viscosity from the data stored in storage portion 204 and the variance of the current through the motor 13 obtained when the impeller 23 position in levitation is changed via the function controlling the impeller position in levitation.

In other words, controller body 201 at storage portion 204 stores data related to a relationship between fluid viscosity and motor current variance corresponding to a previously obtained relationship between fluid viscosity and motor current variance depending on positional change of the impeller in levitation, or correlation data calculated from the data related to such relationship (also serving as data of an expression for viscosity calculation).

As described above, in the embodiment of the present invention a magnetic bearing includes electromagnets each having a magnetic pole and a yoke that are arranged circumferentially. This ensures a large space for winding a coil without increasing the space for the magnetic bearing portion or increasing the size of the pump. Since the coil can be accommodated in such a large space, the electromagnet coil can have an increased winding count and an increased wire diameter and consequently its power consumption can be reduced. Furthermore, the electromagnet can have a yoke in the form of a cylinder or a prism to facilitate winding a coil and thus readily ensure the insulation withstand voltage between the coil and the yoke.

Furthermore, the magnetic bearing portion can have a plurality of electromagnets directly facing a rotative portion to reduce the distance between the rotative portion and the electromagnets corresponding to a plane in which the electromagnetic force of the magnetic bearing acts. Thus, the impeller can be levitated with a reduced amount of current flowing through an electromagnet coil for generating electromagnetic force to levitate the impeller, which is advantageous when the present pump is used as a blood pump since current consumption is one of its significant issues.

Furthermore, the position sensor detecting the impeller position and the impeller can be less distant from each other to enhance the sensitivity of the position sensor.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A magnetically levitated pump comprising:
  a pump portion having a rotative portion provided in a casing and rotated to discharge fluid;
  a rotation driving portion physically out of contact with said rotating portion, coupled with said rotative portion through magnetic force to rotatably drive said rotative portion;
  a position detection portion detecting a position of said rotative portion in levitation; and
  a controlled magnetic bearing portion physically out of contact with said rotative portion, supporting said rotative portion in response to an output corresponding to a result of detection provided by said position detection portion,
  wherein
    said magnetic bearing portion is configured of a plurality of electromagnets formed of a magnetic pole, a yoke and a coil,
    said electromagnets each having magnetic S and N poles, and
    all of said magnetic S and N poles being arranged in a common plane perpendicular to an axis of rotation of said rotative portion at a common radial distance about said axis of rotation.

2. The magnetically levitated pump of claim 1, wherein said rotative portion is provided in a form of a disk having a side facing said rotation driving portion and provided with a permanent magnet, and said rotative portion and said rotation driving portion are magnetically coupled together physically out of contact with each other.

3. The magnetically levitated pump of claim 1, wherein said electromagnet has three pairs of magnetic S and N poles.

4. A magnetically levitated pump comprising:
  a pump portion having a rotative portion provided in a casing and rotated to discharge fluid;
  a rotation driving portion physically out of contact with said rotating portion, coupled with said rotative portion through magnetic force to rotatably drive said rotative portion;
  a position detection portion detecting a position of said rotative portion in levitation; and
  a controlled magnetic bearing portion physically out of contact with said rotative portion, supporting said rotative portion in response to an output corresponding to a result of detection provided by said position detection portion,
  wherein said magnetic bearing portion includes a plurality of electromagnets each directly facing said rotative portion without obstruction by said casing, and
  said rotative portion is provided in a form of a disk having a side facing said rotation driving portion and provided with a first permanent magnet, and said rotation driving portion has a second permanent magnet to face said first permanent magnet, said first and second permanent magnets achieving magnetic-coupling to couple together said rotative portion and said rotation driving portion physically out of contact with each other.

5. A magnetically levitated pump of claim 4, wherein said position detection portion includes a core formed of soft magnetic material and a coil wound around said cores.

6. The magnetically levitated pump of claim 4, wherein any of said electromagnet and said, position detection portion is fixed to said casing by any of welding, brazing, press-fitting, pressure-welding, shrink-fitting and bonding or a combination thereof.

7. The magnetically levitated pump of claim 4, wherein said pump portion has an internal surface coated with heparin.

8. A magnetically levitated pump comprising:
   a pump portion having a rotative portion provided in a casing and rotated to discharge fluid;
   a rotation driving portion physically out of contact with said rotating portion, coupled with said rotative portion through magnetic force to rotatably drive said rotative portion;
   a position detection portion detecting a position of said rotative portion in levitation; and
   a controlled magnetic bearing portion physically out of contact with said rotative portion, supporting said rotative portion in response to an output corresponding to a result of detection provided by said position detection portion,
   wherein said position detection portion includes a magnetic sensor directly facing said rotative portion without obstruction by said casing, and
   said rotative portion is provided in a form of a disk having a side facing said rotation driving portion and provided with a first permanent magnet, and said rotation driving portion ha a second permanent magnet to face said first permanent magnet, said first and second permanent magnets achieving magnetic-coupling to couple together said rotative portion and said rotation driving portion physically out of contact with each other.

9. A magnetically levitated pump of claim 8, wherein said position detection portion includes a core formed of soft magnetic material and a coil wound around said core.

10. The magnetically levitated pump of claim 8, wherein any of said electromagnet and said position detection portion is fixed to said casing by any of welding, brazing, press-fitting, pressure-welding, shrink-fitting and bonding or a combination thereof.

11. The magnetically levitated pump of claim 8, wherein said pump portion has an internal surface coated with heparin.

* * * * *